United States Patent [19]

Nilsson

[11] Patent Number: 5,599,694
[45] Date of Patent: Feb. 4, 1997

[54] PROCESS FOR PRODUCING AN OLIGOSACCHARIDE COMPOUND BY USING GLYCOSIDASES FROM A MOLLUSC

[75] Inventor: Kurt G. I. Nilsson, Lund, Sweden

[73] Assignee: Procur Aktiebolag, Lund, Sweden

[21] Appl. No.: 336,105

[22] Filed: Nov. 4, 1994

Related U.S. Application Data

[63] Continuation of Ser. No. 834,575, filed as PCT/SE90/00537 Aug. 17, 1990, Pat. No. 5,372,937.

[30] Foreign Application Priority Data

Aug. 18, 1989 [SE] Sweden ................................ 8902767

[51] Int. Cl.$^6$ .......................... C12P 19/44; C12P 19/12; C12Q 1/34; C07H 1/00
[52] U.S. Cl. ........................ 435/94; 435/100; 435/101; 435/18; 536/1.11; 536/4.1; 536/17.4; 536/17.6
[58] Field of Search ................ 435/74, 18, 200, 435/240.1, 240.2, 100, 101; 536/4.1, 17.4, 17.6, 1.11

[56] References Cited

U.S. PATENT DOCUMENTS

| 4,918,009 | 4/1990 | Nilsson | 435/73 |
| 5,242,805 | 9/1993 | Naleway | 435/18 |
| 5,246,840 | 9/1993 | Nilsson | 435/101 |
| 5,372,937 | 12/1994 | Nilsson | 435/74 |

FOREIGN PATENT DOCUMENTS

| 470331 | 12/1992 | European Pat. Off. . |
| 4013077 | 4/1990 | Japan . |
| 3-27285 | 3/1991 | Japan . |

OTHER PUBLICATIONS

Paulson et al, "J. of Biological Chem", vol. 253, (16); pp. 5617–5624 (1978).

Johansson et al, "Biotechnology Letters", vol. 8 No. 6, pp. 421–424 (1986).

Primary Examiner—John Kight
Assistant Examiner—Louise N. Leary
Attorney, Agent, or Firm—Beveridge, DeGrandi, Weilacher & Young, LLP

[57] ABSTRACT

Oligosaccharide compounds GlcNAcβ1-3Galβ-OMe, GlcNAcβ1-6Galα-OMe, GalNAcβ1-3Galβ-OMe, GalNAcα1-3Galα-OMe, and Fucα1-6Galβ-OMe.

1 Claim, No Drawings

PROCESS FOR PRODUCING AN OLIGOSACCHARIDE COMPOUND BY USING GLYCOSIDASES FROM A MOLLUSC

This is a continuation of application Ser. No. 07/834,575, now U.S. Pat. No. 5,372,937, filed as PCT/SE90/00537 Aug. 17, 1990.

The present invention relates to a method for enzymatic synthesis of an oligosaccharide compound, which either consists of or is a fragment or an analog of the carbohydrate part in a glycoconjugate. Furthermore, the invention relates to the use of the product prepared by this method. It has been found that the oligosaccharide part of various glycoconjugates (especially glycolipids and glycoproteins) have a number of important functions in vivo (Biology of Carbohydrates, vol. 2, Ginsburg et al., Wiley, N.Y. 1984; The Glycoconjugates, vol. I–V, Academic Press, New York; S. Hakomori, Ann. Rev. Biochem., vol. 50, pp. 733–64); Feizi, Nature, pp. 314, 1985; S. Hakomori, Chemistry and Physics of Lipids, vol 42, pp. 209–33). Among other things it was found that the carbohydrate structures are important for the stability, activity, localisation, immunogenicity and degradation of glycoproteins;

carbohydrates are antigenic determinants (for example blood group antigens);

carbohydrates function as receptors when bound to cell surfaces for pathogens, proteins, hormones, toxins and during cell—cell interactions;

carbohydrates are important for oncogenesis, since specific oligosaccharides have been found to be cancer-associated antigenic determinants;

frequently, only a smaller sequence (di- or trisaccharide) of the carbohydrate part of the glycoconjugate is required for full biological activity (e.g. receptor activity).

Universities and Industry are at present working intensely on developing the use of biologically active oligosaccharides within a number of different fields, such as novel diagnostics and blood typing reagents highly specific materials for affinity chromatography cell specific agglutination reagents targetting of drugs monoclonal antibodies, specific against e.g. cancer-associated structures therapy development of a new type of therapy, as an alternative to antibiotics, based on the inhibition of the attachment of bacteria and virus on cell surfaces with specific oligosaccharides stimulation of the growth of plants and protection against pathogens.

Besides the above mentioned areas, a considerable future market is envisaged for fine chemicals based on biologically active carbohydrates.

About ten different monosaccharides are included in the carbohydrate part of the glycoconjugates: D-glucose (Glc), D-galactose (Gal), N-acetyl-D-glucosamine (GlcNAc), N-acetyl-neuraminic acid (Neu5Ac), D-mannose (Man), L-fucose (Fuc), N-acetyl-D-galactosamin (GalNAc), xylose (Xyl) and arabinose (Ara) (the abbreviations in brackets are according to IUPAC-IUB's abridged terminology for monosaccharides, J. Biol. Chem., vol 257, pp. 3347–3354, 1982, in which publication one also can find the nomenclature used in this text to describe oligosaccharide sequences). The number of possible structures will be almost infinitely great because both the anomeric configuration and the position of the O-glycosidic bond can be varied.

The organic chemical techniques used today for synthesis of these carbohydrate structures require an extensive protective group chemistry with many steps of synthesis and expensive catalysts. Low total yields are obtained in these complicated reaction schemes and the technique is not favorable, especially for larger scale work.

Enzymes are nature's own catalysts with many attractive characteristics, such as high stereo-, regio-, and substrate selectivity as well as high catalytic activity under mild conditions. Today, great hopes are therefore placed in being able to utilise enzymes for large-scale selective synthesis of oligosaccharides with fewer reaction steps and consequently higher total yields than by organic chemical methodology.

Both hydrolases (glycosidases, EC 3.2) and glycosyltransferases (EC 2.4) can be used for synthesis (glycosidases: see Nisizawa et al, in "The Carbohydrates, Chemistry and Biochemistry", 2nd ed vol IIA pp 242–290, Academic Press New York, 1970). With glycosidases reversed hydrolysis (equilibrium reaction) or transglycosylation (kinetic reaction) are often used to obtain synthesis (see e.g. K.G.I. Nilsson, Carbohydr. Res., vol. 167, pp. 95–103, 1987, Trends in Biotechnology., vol. 6, pp. 256–264, 1988).

Reversed hydrolysis:

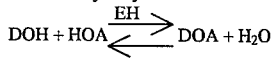

Transglycosylation:

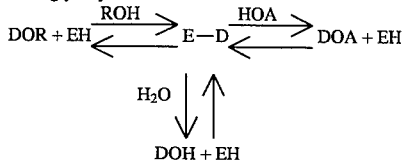

(DOH is donor saccharide, DOR is donor glycoside with α- or β-glycosidically bound aglycon (=R), HOA is acceptor saccharide and EH is enzyme).

With transferases, a nucleotide sugar (UDP-Gal, CMP-Sia, UDP-GalNAc, GDP-Fuc, etc), which is relatively expensive, is used as donor. Furthermore, glycosidases are abundant and can often be used directly without purification. A disadvantage is however that relatively low yields and the wrong product isomers often are obtained. Thus, preponderant formation of 1–6-linkages (i.e. linkages to the primary hydroxyl group of the acceptor) has been obtained, whereas 1–2-, 1–3-, and 1–4-linkages, which are common in glycoconjugates, have been obtained to a less extent.

The present invention allows synthesis of oligosaccharide compounds which previously have not been synthesised with glycosidases. The key to the method is to use glycosidases from molluscs (e.g. squids, clams and mussels) and especially from bivalvia the families "Veneridae " (e.g. "Venus verucosa", "Chamelea gallina", "Tapes pullastra", "Tapes decussatus"), "Mytilidae", "Ostreidae", "Pectenidae" and-"Solenidae". For example, Chamelea gallina contains high amounts of glycosidases, which according to the invention catalyse the synthesis of biologically active carbohydrates in equilibrium or transgycosylation reactions.

The substrates are selected with regard to the oligosaccharide which is to be synthesised, and are often commercially available or can be synthesized by organic or enzymatic methods and therefore do not restrict the use of the invention. The donor and acceptor substrates which are used according to the invention are of the same type which have been used in previous transglycosylation reactions (see for example the articles by K.G.I. Nilsson in Carbohydrate Res. vol. 167 and in Trends in Biotechnology vol. 6, on p. 3 above).

As examples of acceptor substances which can be used with the method according to the invention can be mentioned mono-, di-, or oligosaccharides (or glycosides thereof) in which the carbohydrate part contains one or more of the following monosaccharides: D-glucose, D-galactose, D-mannose, N-acetyl-neuraminic acid, N-acetyl-D-galactosamin, N-acetyl-D-glucosamine and L-fucose, or an analog of these. When the acceptor substance is a glycoside, the aglycone can be a glycosidically bound ($\alpha$- or $\beta$-configuration) aliphatic or aromatic compound (as for example methyl, ethyl, 2-bromoethyl, $(CH_2)_n$COOMe, n>1, allyl or other substances that can be polymerised, benzyl, pentenyl, trimethylsilylethyl, amino acids, derivatives thereof, peptides, derivatives thereof, nitrophenyl, etc). Examples of disaccharides which can be used as acceptors are lactose, GlcNAc$\beta$1-3Gal, Gal$\alpha$1-4Gal, Man$\alpha$1-2Man, GalNAc$\beta$1-3Gal and O-, N-, C-, or S-glycosides ($\alpha$- or $\beta$-configuration) of these as mentioned above.

Other types of aglycons of special interest are amino acids (serine, threonine, hydroxyproline, hydroxylysine, asparagine, etc), peptides, lipids and derivatives or analogs to substances within these three groups. The amino acid and peptide glycosides can be protected on their amino and/or carboxyl groups with the common protecting groups used in peptide synthesis (FMOC, CBZ, BOC, etc). By using such aglycones fragments or analogs of glycoconjugates can be synthesised according to the invention. Moreover, the aglycon can be an amino, nitrile, or an amido group or a fluorogenic substance, or may contain a phosphate, sulphate, or carboxyl group or a derivative thereof. The acceptor substance may also according to the invention consist of a saccharide which has been derivatised in one or more positions besides the 1-position. Such a derivatisation may imply that e.g. one or more hydroxyl groups have been replaced by hydrogen or an organic group. An example of such an acceptor substance is p-nitrophenyl-2-deoxy-$\alpha$-D-galactopyranoside. Another important type of saccharide derivatives consists of substances where the ring oxygen (i.e. the C-5 oxygen of hexoses), has been replaced by sulphur, nitrogen, etc. The glucose analog moranoline, where the C-5-oxygen has been replace by nitrogen is an example of such a derivative. Oligosaccharide analogs that are efficient inhibitors against enzymes or carbohydrate binding proteins may in this manner be synthesised according to the invention.

Products obtained with alkyl glycosides (e.g. methyl-, octyl-, dodecylgoycosides) as acceptor substances may be used as inhibitors in affinity chromatography or in agglutination tests, inhibition-based therapy or for drug-targeting, as structural units for continued enzymatic or organic synthesis, etc. Nitrophenyl glycosides can be simply reduced with, for example, Pd/C to aminophenyl glycosides, which, directly or after chemical modification, can be coupled covalently to different polymers (agarose, cellulose, dextran, polyethylene glycol, silica, etc) as well as to enzymes, peptides, proteins, lipids or analogs thereof, etc (Methods in Enzymology, Academic Press, volumes 34, 44, 50 and 104). Moreover, the amino group is readily. converted to several other reactive groups, such as diazo, N-bromoacetate, isothiocyanate, etc. Other groups which, directly or after chemical modification can be used as a so-called spacer arm (Methods in Enzymology, vol. 34) in the same way as described above for the aminophenyl group and which can be used as aglycon according to the invention are for example 2-aminoethyl and 6-aminohexyl, 2-bromoethyl, 2-(2-carbomethoxyethylthio) groups or derivatives thereof. Glycosides with a polymerisable aglycon as for example 2-hydroxyethylmethacrylate may also be used as acceptor substances. As an example of a N-glycosidically bonded aglycon, 6-aminocaproic acid amide (-NHCO($CH_2$)$NH_2$) may be mentioned.

The donor substrates which can be used with the method according to the invention are the same as those employed in previous methods involving enzymatic transglycosylations (see references on p. 3 above) and thus do not limit the scope of the invention.

As examples of donor substances that can be used with the method according to the invention may be mentioned monosaccharide-glycosides and di- or oligosaccharides (or glycosides thereof) in which the carbohydrate part contains one or more of the monosaccharides D-galactose, D-glucose, D-mannose, N-acetyl-neuraminic acid, N-acetyl-D-galactosamin, N-acetyl-D-glucosamine and L-fucose. As examples of suitable glycosyl donors may be mentioned the nitrophenyl $\alpha$- or $\beta$glycosides of the monosaccharides above, lactose, dimannose and raffinose. As examples of suitable donor substances for endoglycosidases may be mentioned nitrophenyl derivatives of biologically active carbohydrate sequences (e.g. Gal$\beta$1-3GlcNAc$\beta$-OPhNO$_2$-p), biologically active oligosaccharides or structures of the type Glc($\beta$1-3Glc)$_n$ $\beta$1-3Glc (n>1).

The concentration of the glycosyl donor in the reaction mixture is selected with regard to the oligosaccharide which is to be synthesised and also with regard to the properties of the enzyme and therefore do not restrict the use of the invention. In general, addition of the donor in smaller portions may be advantageous in order to minimise the risk that the donor also acts as an acceptor (unless this is desired).

The enzymes are selected primarily with regard to which oligosaccharide is to be synthesised. The enzyme may be used in situ or after partial or complete purification from their natural environment. The enzyme may be used in soluble form or immobilised to a solid support by e.g. adsorption, encapsulation, chelation, precipitation or covalent binding.

Examples of $\alpha$- and $\beta$-glycosidases which may be used according to the invention are D-mannosidases, D-galactosidases, L-fucosidases, N-acetyl-D-galactogaminidages, hexosaminidases and other glycosidases of EC group 3.2 (Enzyme Nomenclature, Academic Press, 1984). Both endo- and exoglycosidases may be used with the method according to the invention.

The degree of purity of time enzyme employed is not critical. The enzyme may be used in situ or after complete or partial isolation from its natural biological environment. Also, a crude extract of the organism or a tissue thereof may be used. The enzyme may also have been obtained after precipitation with e.g. ammonium sulphate. The enzyme may be present in crystalline form or be enclosed within micelies. The biochemical literature is rich in detailed information about the purification and isolation of glycogidases. The enzyme may be produced with recombinant techniques. Then, if desired, one or more of the amino acids in the amino acid sequence of the enzyme may be changed in order to optimise the properties of the enzyme, e.g. thermostability, catalytic efficiency and/or regioselectivity.

The enzyme may be used in soluble form or may be immobilised by e.g. adsorption, encapsulation, chelation, precipitation or covalent binding to a solid support, such as a polymeric substance, or a derivative thereof which is insoluble in protic or aprotic solvents (Methods in Enzymology, vol. 44, Academic Press, 1976). The form selected is not critical to the invention. If the enzyme is used in soluble form, it may first have been chemically modified in a suitable manner in order to e.g. increase the thermostability or the stability in organic cosolvents. Enzyme immobilised to an insoluble polymer comprising, for example, agarose, cellulose, hydroxyethyl acrylate, glass, silica, polyacrylic amide, polyacrylate-based plastics, etc., is readily separated from the product mixture, and the enzyme may thus be reused. An additional advantage is that in many cases a certain stabilisation against elevated temperatures and organic cosolvents is obtained.

The synthetic method according to the invention can be carried out under highly diverse conditions as regards, for example, pH, type of buffer, temperature and concentration of the reactants. Various cosolvents (acetonitrile, N,N-dimethyl formamide, dimethyl sulphoxide, dioxane, ethanol, ethylene glycol, methanol, pyridine, tetrahydrofurane, etc) may be used and in varying concentrations together with water. Moreover, the reactions can be carried out in two-phase system, water-organic solvent (chloroform, cyclohexane, methylene chloride, etc). The enzyme may then be enclosed in reversed micelles (P. Luisi, Angew. Chem., vol. 97, pp. 449–60, 1985). The reactions can also be carried out in organic solvent with precipitated enzyme (Kazandjian et al, J. Amer. Chem. Soc., vol. 107, 1985). The reaction conditions are not critical but are selected primarily on the basis of the properties of the reactants employed in the synthesis concerned, and also on the basis of practicality. For example, it may be mentioned that it is usually convenient to use room temperature with enzymes and, in the case of water-rich medium, the pH is usually in the range 4–11. Organic cosolvents may be used to minimise the hydrolytic side-reaction. For the same reason, two-phase systems may be used. In some cases, however, considerably higher yields are obtained in water without cosolvents added.

The temperature may also be varied to influence product yield and the stability of the enzyme. The temperature most frequently used lies in the range 5°–55° C., but higher temperatures can be used with thermostable glycosidases and with enzymes stabilised against thermal denaturation with for example, high substrate concentrations (Johansson et al, Biotechnol. Lett., 8 (1986) 421–424). Advantages with high temperatures are, for example, that high substrate concentrations may be used, which reduces the water activity and thus increases the yield of product. Another advantage is that the activity of the enzyme increases, which means shorter reaction times at increased temperatures. One advantage with this is that glycosides, e.g. methyl or ethyl glycosides, which are hydrolysed slowly at room temperature can be used as suitable glycosyl donors at increased temperatures (50°–60° C.). The upper temperature limit is determined by the thermostability of the enzyme in the reaction medium. For some transglycosidations, a lower temperature was found to give a higher yield of product glycoside.

Normally, relatively high concentrations of donor and acceptor substances are used to obtain maximum yield of product. This means usually 0.1–1 M concentration of nitrophenyl glycosides and 0.2–7 M concentration of methyl glycosides. In general, high concentrations of substrates are obtained by shortly heating the reaction mixture to near the boiling point, allow the solution to cool to 37°–75° C. (depending on the thermostability of the enzyme) and then add the enzyme. Cosolvents can be used to increase the solubility of glycosides with a hydrophobic aglycon, e.g. p-nitrophenyl glycosides:

The reaction can be monitored by means of TLC, HPLC, or by spectrophotometric measurement of liberated aglycon (e.g. p-nitrophenol, 400 nm). When maximum yield of the product glycoside has been obtained the reaction is terminated by denaturation of the enzyme by changing the pH, increasing the temperature and/or adding organic cosolvent (such as ethanol). Heating to 80°–85° C. for 3–5 min, followed by addition of ethanol to a concentration of about 80%, usually is sufficient.

Various techniques may be used for isolation of the product. Precipitation with e.g. an organic solvent such as ethanol is useful, especially when an excess of one of the reactants is used or when the donor, acceptor or products have different solubilities. After the equilibrium controlled synthesis or the transglycosylation reaction and after e.g. heat treatment as above and dilution of the reaction mixture, it can be useful to add a second glycosidase, which has a different regioselectivity than the glycosidase used in the synthesis. In this way, unwanted regioisomers (for example with 1-6-linkages) may be more or less selectively hydrolysed, which facilitates isolation of the desired product. Precipitation and hydrolysis of byproducts are complementary to chromatography (adsorption chromatography, gel filtration with for example, Sephadex® G10-G25, HPLC with, for example, amino-silica, reversed phase silica or the new Dionex® columns). Useful is, for example, column chromatography with e.g. methylene chloride:methanol:water (e.g. 6:4:1; V/V/V) as eluent and silica as solid phase, followed by drying at low pressure and acetylation with acetic anhydride and pyridine (e.g. 1:1; V/V) of the partially purified product glycoside. A new column chromatographic step (silica, eluent for example ethyl acetate:isooctane) usually gives a pure acetylated product. Deacetylation in dry methanol with a catalytic amount of natrium methoxide frequently gives pure and crystalline product. Isolation of products with hydrophobic aglycons (e.g. nitrophenyl oligosaccharides) may frequently be carried out in one step with preparative HPLC-equipment and $C_{18}$-silica.

The synthesis method according to the invention is generally applicable to the synthesis of oligosaccharide sequences included in glycoconjugates (see examples of structures given in references on page 1 above and in the Tables below). Of special interest are the minutest fragments of these structures, which are sufficient to transfer biological activity and the choice of donor and acceptor in the equilibrium or transglycosylation reaction is determined by this.

Examples of interesting structures are blood group determinants, cancer-associated oligosaccharide structures and structures with biological receptor activity (see references on page 1 above).

Examples of biologically active carbohydrates which are of interest to synthesise parts of or completely are found in the Tables below.

TABLE 1

Examples of carbohydrate structures of glycolipids.

Ganglio Series

Neu5Ac$\alpha$2—3 Gal$\beta$1—3 GalNAc$\beta$1—4 Gal$\beta$1—4 Glc$\beta$1—1Cer     GM$_{1b}$

TABLE 1-continued

Examples of carbohydrate structures of glycolipids.

GalNAcβ1—4 Galβ1—4 Glcβ1—1 Cer      $GD_2$
|
Neu5Acα2—8 Neu5Acα2[3]

Globo Series

GalNAcβ1—3 Galα1—4 Galβ1—4 Glcβ1—1 Cer      Globoside

Lacto Series

Fucα1—2 Galβ1—4 GlcNAcβ1—3 Galβ1—4 Glcβ1—1 Cer      Lacto-fucopentaosylVCer

Muco Series

GalNAcα1—3 Galβ1—3 Galβ1—4 Glcβ1—1 Cer

Gala Series

Galα1—4 Galβ1—1 Cer      Galabiose

TABLE 2

Examples of carbohydrates structures (N- or O-bound) of glycoproteins.

Oligomannosidic Type

```
Manα1- 2 Manα1 - 2 Manα1
                        | 6
                     Manα 1
                     | 3  | 6
      Man α1 - 2 Manα1        Manβ1 - 4 GlcNAcβ1 - 4GlcNAcβAsn
                           | 3
         Man α1 - 2 Manα1
```

Complex (N-acetyllactosamine) Type

```
Neu5Acα2 -6 Galβ 1 - 4 GlcNAcβ1 - 2 Manα1
                                         | 6
                                     Manβ1 - 4 GlcNAcβ1 - 4 GlcNAcβAsn
                                         | 3
Neu5Acα2 - 6 Galβ 1 - 4 GlcNAcβ1 - 2 Manα1
```

Hybrid Type

```
Neu5Acα2 - 6 Galβ1 - 4 GlcNAcβ1 - 2 Manα1
                                           | 6
Neu5Acα2 - 6 Galβ1 - 4 GlcNAcβ1 - 2 Manα1      Manβ1 - 4 GlcNAcβ1 - 4 GlcNAcβAsi
                                         | 4   | 2
                                         Manα1
                                         | 2
     Neu5Acα2 - 3 Galβ1 - 4 GlcNAcβ1
```

O-Bound

```
              Neu5Acα2
                 | 6
Neu5Acα2 - 3 Galβ1 - 3 GalNAcαThr/Ser

GalNAcα1 - 3(Galβ1 - 4GlcNAcβ1 - 3)₂Galβ1
                                        | 3
                                    GalNAcαThr/Ser
                                        | 6
     Fucα1 - 2 Galβ1 - 4GlcNAcβ1
```

TABLE 3

Examples of blood group structures of humans.

| Blood group | Structure |
|---|---|
| A | GalNAcα1—3Galβ1—<br>\|<br>Fucα1² |
| B | Galα1—3Galβ1—<br>\|<br>Fucα1² |
| H | Fucα1—2Galβ1— |
| Le$^a$ | Galβ1—3GlcNAc—<br>\|<br>Fucα1⁴ |
| Le$^b$ | Galβ1—3GlcNAc<br>\|       \|<br>Fucα1²  Fucα1⁴ |
| P₁ | Galα1—4Galβ1—4GlcNAcβ1—3Galβ1—4Glcβ1— |
| P | GalNAcβ1—3Galα1—4Galβ1—4Glcβ1— |
| pk | Galα1—4Galα1—4Glcβ1— |
| p | Galβ1—4Glcβ1— |

TABLE 4

Examples of cancer-associated carbohydrate antigens.

| | | |
|---|---|---|
| Galα1-4 Galβ1-4 Glcβ | Gb₃ | Burkitt Lymphoma |
| Galβ1-4(Fucα1-3)GlcNAc | Le$^x$ | Colorectal cancer |
| [Galβ1-4(Fucα1-3)GlcNAcβ1-3]₃Galβ | poly-Le$^x$ | Human adenocarcinoma |
| Galβ1-3 GalNAcα | T antigen | Several cancers |
| GalNAcα1-3 GalNAcβ1-Hex ... | Forssman antigen | Tumors from Forssma negative patients |
| GalNAcα1-3 Hex-HexNAc ... | Blood group A-like antigen | Blood group B and O -individuals |
| Neu5Acα2-8 Neu5Acα2-3 Galβ1-4 Glc | (GD₃) | Human melanoma |
| Neu5Acα2-3 Galβ1-3(Fucα1-4)GlcNAc | Sia-Le$^y$ | Colon pancreas cancer |

| Strain (organism)/adhesin Site of infection | Suggested specificity |
|---|---|
| E. coli type 1 fimbriae Human urinary tract | Man |
| F-fimbriae | Galα1—4Galβ—O |
| Human urinary tract X-fimbriae | NeuAcα2—Gal, GlcNAcβ1—O— |
| K88 pig, small intestine | Galα1—3Gal—α1—O |
| K99, calf, small intestine | GalNac, NeuAc |
| Shigella-toxin | Galαγ—4Gal—terminal position |
| S. saprophyticus Human urinary tract | Galβ1—4GlcNAcβ—O |
| S. pneumococcus Human respiratory tract | GlcNAcβ1—4GlcNAc—OH<br>GlcNAcβ1—3Galβ—O |
| M. pneumoniae Human respiratory tract | Lactosamine 1 |

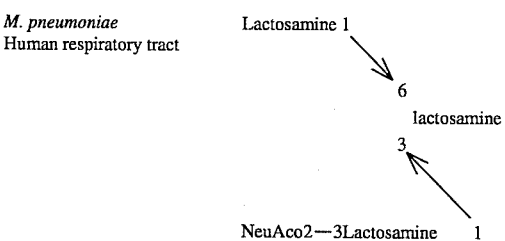

| Strain (organism)/adhesin Site of infection | Suggested specificity |
|---|---|
| Influenza virus Human respiratory tract | NeuAc—Gal |
| Vibrio cholera and piliated gonococcus Intestine/human urinary tract | Galβ1—3GalNAcβ1—4Galβ1—4Glc (GM₁)<br>3<br>↑<br>1<br>NeuAc |

Some examples of how the invention may be used in actual practice are described in the following Examples, which, however, are in no way intended to restrict the scope of the invention (abbreviations according to IUPAC-IUB's recommendations, J. Biol. Chem., vol. 257, pp. 3347–3354, 1982).

EXAMPLE

The mollusc "chamelea gallina" was obtained at a local shop in southern Spain. The livers were homogenised, extracted with distilled water and the material in the supernatant was fractionated with ammonium sulphate as described by Reglero and Cabezas (Eur. J. Biochem. vol. 66, pp. 379–387, 1976). The precipitate was used for the syntheses described in,he Examples below. The reactions in the Examples below were followed by HPLC (eluent acetonitrile-water; 70–30; V/V; amino-silica as adsorbent) and by measuring the amount of liberated nitrophenol (absorbance at 405 nm). Solvents were removed with a rotary evaporator and then at low pressure. The products were isolated by column chromatography (Sephadex® G10 followed by semipreparative HPLC; eluent water-acetonitrile, 30–70, V/V; amino-silica as adsorbent) and crystallised from ethanol. The products were characterised with NMR (13C and 1H-spectra).

Example 1

Synthesis of Methyl 3-O-(2-acetamido-2-deoxy-β-D-glucopyranosyl)-β-D-galactopyranoside (GlcNAcβ1-3Galβ-OMe): To a mixture of GlcNAcβ-OPhNO₂-p (0.34 g), Galβ-OMe (2.0 g), 0.03 M natrium citrate/phosphate buffer (20 ml), pH 5.8, was added the above mentioned (see "EXAMPLE") ammonium sulphate precipitate (100 mg) from "Chamelea gallina" which contained N-acetyl-β-D-glucosaminidase. The mixture was agitated gently at 37° C. After 80 hours, the reaction was stopped by heating for ca 5 minutes at 80° C. Isolation of the product, employing Sephadex® G10 and HPLC as described above (see

Example"), gave crystalline product which was characterised with NMR.

Example 2

Synthesis of GlcNAβ1-6Manβ-OMe: This substance was synthesised and isolated in the same manner as GlcNAcβ1-3Galβ-OMe, except that 0.68 g GlcNAcβ-OPMNO$_2$-p and 2 g Manα-OMe were used as substrates and that the reaction was carried out in 19 ml of the above buffer and 1 ml of N,N-dimethylformamid. After 65 hours at room temperature, the reaction was stopped as above and the product isolated with Sephadex® G10 and HPLC as described above (see "EXAMPLE"). The product was characterised with NMR.

Example 3

Synthesis of GlcNAcβ1- 6Galα-OMe ((Methyl 6-0-(2-acetamido-2-deoxy-β-D-glucopyranosyl)-α-D-galactopyranoside)): The synthesis and the isolation of the product were carried out as described for GlcNAcβ1-3Galβ-OMe in Example 1 above, using 0.34 g GlcNAcβ-OPhNO$_2$-p and 2 g Galα-OMe in 19 ml of the citrate/phosphate buffer (pH 5.8) and 1 ml N,N-dimethylformamide and with 100 mg ammonium sulphate precipitate from "Chamelea gallina". After 65 hours at room temperature, the reaction was stopped as in Example 1 and the product isolated by Sephadex® G10 followed by HPLC as described under "EXAMPLE" above.

Example 4

Synthesis of Methyl 3-O-(2-acetamido-2-deoxy-β-D-galactoopyranosyl)-β-D-galactopyranoside (GalNAcβ1-3Galβ-OMe): This structure was synthesised and isolated in analogy with that described in Example 1, using 0.5 g GalNAcβ-OPhNO$_2$-p, 2.5 g Galβ-OMe in 20 ml sodium phosphate buffer (pH 5.8) and 100 mg of the ammonium sulphate precipitate from "Chamelea gallina", After 5 days reaction at room temperature, the reaction was stopped as above and the product isolated with Sephadex® G10 followed by HPLC as described above.

Example 5

Synthesis of Methyl 3-O-(2-acetamido-2-deoxy-α-D-galactopyranosyl) α-D-galactopyranoside (GalNAcα1-3Galα-OMe): The synthesis and the isolation of the product were carried out with the ammonium sulphate precipitate as described for GlcNAcβ1-3Galβ-OMe in Example 1, but with GalNAcα-OPhNO$_2$-p, (70 mg) and Galα-OMe (1 g) as substrates.

Example 6

Synthesis of Fucα1-6Galβ-OMe: The synthesis was carried out as in Example 1 above, but with 0.4 g Fucα-OPhNO$_2$p and 2 g Galβ-OMe as substrates in 0.05 M sodium acetate buffer (20 ml), pH 5.5) at 37° C. and with 0.5 g ammonium sulphate precipitate from "Chamelea gallina". After reaction for 70 hours, the product was isolated by the following procedure: column chromatography (Sephadex® G10), the disaccharide fractions were evaporated and acetylated (pyridine-acetic acid), column chromatography on Kisel gel 60 (eluent toluene-ethyl acetate, 1:1; V/V) gave pure acetylated Fuc 1-6Galβ-OMe, which was deacetylated with sodium methoxide to give the title compound.

Example 7

Synthesis of GlcNAcβ1-3Galβ-OMe: Galβ-OMe (1.4 g) was dissolved in 1 ml 0.04 M sodium phosphate buffer, pH, 6.0, by the gradual addition of the glycoside to the buffer at 95°–100° C. GlcNAcβ-OPhNo$_2$-p (100 mg) was added and after cooling to 55° C., the ammonium sulphate precipitate obtained from the bivalve "Chamelea gallina" was added (see the Swedish patent application no 8902767-6). After 34 hours at 55° C., the reaction was stopped by heating at 90° C. and the product was isolated by chromatography (Sephadex® G10 and amino-silica, HPLC).

Example 8

Synthesis of GalNAcα1-3Galα-OMe: Galα-OMe (1 g) was dissolved in 1 ml sodium phosphate/citrate buffer, pH 5.0, as above and GalNAcα-OPhNO$_2$-o (50 mg) was added. After cooling to 55° C. the bivalve preparation (60 mg) was added and the reaction was carried out as in the above example.

The technique with high substrate concentration described above is used for the synthesis of Fucα1-6Galα-OMe, GalNAcβ1-3Galβ-OMe, GlcNAcβ1-6Galα-OMe, GlcNAcβ1-6Manα-OMe and other oligosaccharides with the above bivalve preparation.

I claim:

1. An oligosaccharide compound selected from the group consisting of GlcNAcβ1-3Galβ-OMe, GlcNAcβ1-6Galα-OMe, GalNAcβ1-3Galβ-OMe, GalNAcα1-3Galα-OMe, and Fucα1-6Galβ-OMe.

* * * * *